United States Patent [19]

Kang, Kenneth S.

[11] 4,259,477

[45] Mar. 31, 1981

[54] PROCESS FOR MAKING CELLULASE-FREE XANTHAN GUM

[75] Inventor: Kang, Kenneth S., Lajolla, Calif.

[73] Assignee: Merck & Co., Inc., Rahway, N.J.

[21] Appl. No.: 45,151

[22] Filed: Jun. 4, 1979

[51] Int. Cl.³ .............................................. C08B 37/00
[52] U.S. Cl. .................................... 536/114; 424/49; 424/780
[58] Field of Search ................... 536/114, 51; 424/180

[56] References Cited

U.S. PATENT DOCUMENTS

| 3,516,983 | 6/1970 | Colegrove | 536/114 |
|---|---|---|---|
| 3,919,189 | 11/1975 | Empey et al. | 536/114 |
| 4,070,535 | 1/1978 | Empey et al. | 536/114 |

OTHER PUBLICATIONS

Chemistry and Industry of Starch; R. W. Kerr, ed. Academic Press, 1944 (p. 237).

*Primary Examiner*—Johnnie R. Brown
*Assistant Examiner*—Blondel Hazel
*Attorney, Agent, or Firm*—Gabriel Lopez; Hesna J. Pfeiffer; Julian S. Levitt

[57] ABSTRACT

Cellulase in xanthan gum can be completely destroyed by treating xanthan gum beer with about 0.08 to 0.1% alkali metal hypochlorite followed by heat treatment.

4 Claims, No Drawings

PROCESS FOR MAKING CELLULASE-FREE XANTHAN GUM

BACKGROUND OF THE INVENTION

Xanthan gum has been found to be useful in an increasingly large number of applications in the food and industrial fields. This is true when the gum has been used primarily by itself but also when in combination with other active ingredients. In many such cases, synergistic effects have been observed which make certain unique gum blends particularly useful for certain operations. One limitation on further applications has been the presence of the enzyme cellulase in normally produced xanthan gum. This enzyme limits the practical use of xanthan gum in combination with cellulose or cellulosic compounds such as carboxymethyl cellulose and hydroxyethyl cellulose.

In the past, attempts to remove cellulase from xanthan gum have included (1) treating fermentation beer with mercurial compounds at high temperature, (2) treating xanthan gum presscakes with propylene oxide, and (3) heating high pH xanthan beer to about 93° C. followed by cooling and neutralization. This last technique is not always reliable and also results in about a 10% loss of product.

U.S. Pat. No. 3,516,983 describes a process for removing proteinaceous impurities from xanthan beer by treating said beer with alkali metal hypochlorites at elevated pH followed by acidification and precipitation with a lower alcohol.

SUMMARY OF THE INVENTION

It has now been found that a cellulase-free xanthan gum can be produced by treating xanthan gum beer with an alkali metal hypochlorite at an initial level of 0.08% to 0.1 weight %. At pH 6.0 to 7.0 the treatment pH lasts for 6–8 hours at about 30° C. It is preferred to then heat said treated beer at 85° C.–95° C. for several minutes. This treatment is followed by recovery of the enzyme-free gum as by precipitation with a lower alcohol, drying, and milling.

This process is economic, simple, and reliable. Further, it does not require neutralization and does not cause the rheological changes observed with prior art processes for achieving a cellulase-free xanthan gum such as in U.S. Pat. No. 4,070,535.

DETAILED DESCRIPTION OF THE INVENTION

By xanthan gum is meant the extra-cellularly produced gum made by the heteropolysaccharide-producing bacterium *Xanthomonas campestris* by the whole culture fermentation of a medium comprising a fermentable carbohydrate, a nitrogen source, and other appropriate nutrients. Processes for producing xanthan gum are well-known (e.g. U.S. Pat. No. 3,433,708). Xanthan gum beer, which is a commercially available product, is the post-fermentation contents of xanthan fermentation vats prior to recovery of the gum.

The best evidence presently available suggests that xanthan gum has the formula:

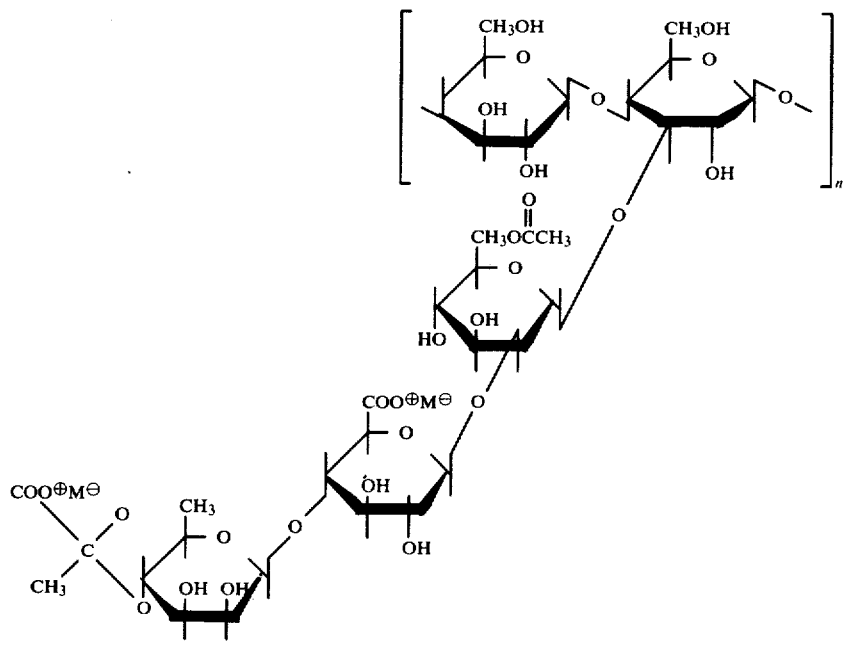

wherein $M^{\oplus}$ is $Na^+$, $K^+$, or $\frac{1}{2} Ca^{++}$. Estimates of the molecular weight range from 2–50 million. The organism Xanthomonas produces this gum as an acid which is then converted to a salt in the fermentor, the ratio $Na^+:K^+:Ca^{++}$ in the recovered gum depending on the fermentation media conditions.

As indicated above, production of the acid form of xanthan gum by *Xanthomonas campestris*, NRRL B-1459, under a variety of fermentations conditions is well known. The inventive feature of this application relates to the post-fermentation treatment of xanthan gum beer with alkali metal hypochlorite, which is independent of the biosynthetic pathway of the Xanthomonas organism in its production of the acid form of xanthan gum. A proprietary mutant strain of *X. campestris* is known by applicant's assignee to produce the acid form of xanthan gum in somewhat higher yields than does B-1459. It would be apparent to one skilled in the art that either B-1459 or said proprietary mutant strain could be used in the practice of this invention. Since the function of the microorganism is merely to produce the acid form of xanthan gum, availability of this mutant strain is not significant to the practice of this invention.

In the process of this invention, xanthan beer is treated with any acid, preferably $H_2SO_4$, or any base, preferably NaOH, whichever is necessary to adjust the pH to 6.0 to 7.0. This pH range is recommended for purposes of conserving hypochlorite. Although the process will work over the range pH 3.0 to 10.0, after hypochlorite treatment but prior to heating the pH range is adjusted to 5.0 to 7.0 such that the final recovered product has a pH of 6.0 to 8.0, which is the preferred pH.

When the proper pH level is reached, an alkali metal hypochlorite, such as KClO or LiClO but preferably NaClO, is mixed into the beer to a final NaClO concentration of 0.08%–0.1% on a weight/weight basis. (An alternate process would be to bubble $Cl_2$ gas into the beer at a pH above 8.) As NaClO is an oxidizing agent, levels above 0.1% are not recommended. NaClO levels below 0.08% do not completely destroy the enzyme. This mix is allowed to sit at 30° C.±2° till the hypochlorite level is less than about 0.03% but preferably less than 0.02%. For mixes with initial hypochlorite levels of 0.08% at pH 6.0 to 8.0 this occurs in about 6–8 hours. Heat treatment can be started when the hypochlorite level is less than about 0.03%, preferably about 0.02%. This level is determined according to Test Method I.

TEST METHOD I

Procedure for the Determination of Hypochlorite in Fermentation Beer

A. Reagents 1. 20% Potassium Iodide. 20 g of KI reagent grade per 80 ml distilled water.
2. 5 N Sulfuric Acid. 13.9 ml of concentrated $H_2SO_4$ per 100 ml distilled water.
3. 0.1 N Sodium Thiosulfate. 15.8 g $Na_2S_2O_3$ reagent grade (anhydrous) per 1000 ml.
4. Bleach. 5.25% hypochlorite.

B. Determination of % $OCl^-$ in a Concentrated Bleach Solution

Pipet 5 ml of the bleach solution into a beaker. Add 100 ml. D.I. water. Add 10 ml of 20% KI and 10 ml of 5 N $H_2SO_4$. Titrate solution to a colorless end point with 0.1 N $NaS_2O_3$.

$$\% \text{ OCl}^- = \frac{(0.1 N) \times \text{Volume of Thiosulfate Soln (ml)}}{(5 \text{ ml})\left(\frac{10}{37.25^*}\right)}$$

*equivalent weight of NaOCl.

$\% \text{ OCl}^- = 0.0745 \times \text{Volume of Thiosulfate Soln (ml)}$

C. Determination of % $OCl^-$ in Fermentation Beer

1. Prepare a 0.08% (0.0107 M, 0.0214 N) sodium hypochlorite solution by dilution of bleach solution (e.g. Sunnysol). Dilute a 50 ml sample with 200 ml D.I. water.
2. Add 10 ml of 20% KI and 10 ml of 5 N $H_2SO_4$.
3. Titrate this solution with 0.1 N $Na_2S_2O_3$ solution to a colorless end point. Record reading (volume A). Theoretical is 10.7 ml.
4. Adjust beer solution to required initial level of hypochlorite (e.g. 0.03% to 0.08% etc.).
5. To samples (50 gm) add 200 ml D.I. water with stirring, 10 ml of 20% KI, and 10 ml of 5 N $H_2SO_4$.
6. Titrate with 0.1 N $Na_2S_2O_3$ (volume B), color changing from brown (iodine color) to white.

D. Calculations $\% \text{ OCl}^- = (B/A) \times 0.08\%$

Where the initial hypochlorite level is above about 0.1%, extremely long times are required to get readings below 0.02%, during which oxidation of the xanthan gum itself takes place. Likewise, if heat treatment takes place when the hypochlorite level is above about 0.03%, oxidation of the gum occurs.

When the hypochlorite reaches the 0.02% level, the beer is heated to 85°–95° C. for a period of 2–10 minutes, following which the regular processes of recovery, as from lower alcohol, drying, milling, etc., may be performed. Enzyme destruction is essentially complete after NaClO treatment, however, heat treatment ensures its complete destruction. A gum can be tested for cellulase activity according to Test Method II.

TEST METHOD II

Test for Cellulase

1. Preparation of HEC[1] Substrate Solution A citrate buffer is prepared by dissolving 5.25 gm of citric acid in 50 ml of 1 N NaOH and diluting this solution to a volume of 250 ml.

[1] Hydroxyethyl cellulose-Union Carbide.

To prepare 2 liters of the HEC substrate solution, 32 ml of 0.1 N NaOH and 48 ml of the citrate buffer are added to 1920 ml of distilled water. This solution is heated and while heating 4 gm of Dowicil 100 are added and mixed in. When this solution is hot (70°–80° C.) 40 gm of HEC (QP4400) are added amd mixed in vigorously with a Lightnin Mixer. The solution is then allowed to sit (usually overnight) to cool and to allow the air bubbles to rise. Every precaution should be taken to prevent contamination of this solution by cellulase positive substances.

2. Prepare in distilled water 1% solutions of all gum samples to be tested as well as a 1% solution of a known cellulase positive sample.

3. Prepare the screw-top plastic jars by washing them well in hot water and rinsing them with distilled water. The jars are then wiped dry.

4. Prepare negative controls by adding 120 ml of the HEC solution to two of the plastic jars. Prepare the test samples by adding 30 mls of the gum solution to 90 ml of the HEC solution. Mix it in with a Lightnin Mixer. The stirring blade should be thoroughly cleaned after each sample to avoid contamination. The positive control is prepared by adding 30 ml of the cellulase positive solution to 90 ml of the HEC solution and mixing it in. The positive control is always prepared last. All samples are done in duplicate.

5. Measure the temperature of the negative control jar.

6. Measure the viscosity and pH of all samples. The negative control must always be measured first, followed by the test samples. The positive control is always measured last. All surfaces including pH probes spatulas and Brookfield spindles must be meticulously cleaned for each sample to prevent cross-contamination. The viscosity is measured at 60 rpm using the No.

4 spindle and each sample is stirred lightly with a spatula before measuring the viscosity.

7. After the viscosity of the samples have been measured, the caps are tightened and the jars are incubated at 43°–44° C. for four days. Viscosity and pH measurements should be taken at least twice during this period, preferably the 2nd and 4th day. When this is done, the samples are cooled to the temperature recorded for the negative control before measuring. This is important as the HEC viscosity is highly temperature sensitive.

8. At the end of four days, the results are interpreted as follows. If the average viscosity of a test sample decreases by more than 7% from the average viscosity of the negative control, the sample is regarded as cellulase positive. If the viscosity of the sample is equal to the negative control or the decrease in viscosity is less than 7%, then the sample is regarded as cellulase negative.

The cellulase-free xanthan gum produced by the process of this invention is useful as a rheology modifier in food and nonfood products either by itself or in combination with other compounds, specifically with other gums. Of particular importance, this cellulase-free gum can be combined with cellulosic compounds, particularly carboxymethyl cellulose to form stable blends. One such blend would be useful as a toothpaste.

The invention is further described in the following examples which are intended to be illustrative and not limiting.

EXAMPLE 1

Non-Heat-Treated Beer 800 ml of xanthan gum beer having a viscosity of 5750 cP are treated with 0.1% NaClO (0.66% Sunny Sol, a 15% NaClO solution) for 3 hours. Xanthan gum is precipitated out of a 400 ml aliquot of the treated beer and shows no cellulase activity.

Although this treatment produces a cellulase-free xanthan gum, the product is unstable because of the high levels of residual hypochlorite. A holding time of 6–8 hours is necessary to reduce the residual hypochlorite to the preferred 0.2% level.

EXAMPLE 2

0.08% Hypochlorite and Heat Treatment

Sodium hypochlorite solution (5.25%, 19.6 g) is added to three samples of xanthan fermentation beer (1233 g) at 30° C. The initial treatment level is 0.08% hypochlorite. The pH of these samples is adjusted to 5, 6, and 7 with 5 N $H_2SO_4$. After 5.5 hours at room temperature, the hypochlorite levels are monitored. Calculations show that hypochlorite levels drop to 0.020, 0.017, and 0.016%, respectively. After approximately six hours of storage, the samples are heated to 90° C. The samples are precipitated with alcohol (2.5×volumes), dried, and milled.

The cellulase activity of these samples is determined using Kelco Test Method II. All samples are cellulase free, as shown in Table 1. Viscosities are measured on a Brookfield LVF viscometer, 60 rpm, spindle 4. It should be noted that the increase in viscosity for some samples is expected, indicating that hydration has continued during the 6 hours of storage.

TABLE 1

| | | Cellulase Test Results | | | |
|---|---|---|---|---|---|
| | | Viscosity (cP) | | | Average |
| | | Original | Final | % Change | % Change |
| HEC Negative | A | 3550 | 3580 | +1 | +3.5 |
| Control | B | 3590 | 3818 | +6 | |
| pH 5 Sample | A | 2770 | 2820 | +2 | −2 |
| | B | 2890 | 2780 | −4 | |
| pH 6 Sample | A | 2600 | 2670 | +3 | 0 |
| | B | 2650 | 2580 | −3 | |
| pH 7 Sample | A | 2780 | 2810 | +1 | +1 |
| | B | 2750 | 2780 | +1 | |

EXAMPLE 3

0.1% Hypochlorite and Heat Treatment

A batch of xanthan gum fermentation beer is produced in a 1,000-gal fermentor. The beer pH is approximately 6.5. A solution of sodium hypochlorite is mixed into the beer to a final concentration of NaClO of 0.1% on a weight/weight basis. This mixture is allowed to sit for 6 hrs at 30°–31° C. At this point, the concentration of NaClO is approximately 0.03%. The reacted beer is heat-treated at 90°–95° C. for 10–12 minutes. Xanthan gum is recovered by precipitation using isopropyl alcohol followed by drying and milling. The test results of cellulase activity in the gum are shown in Table 2. The positive control uses regular xanthan gum.

TABLE 2

| | Cellulase Test Results | | | | | |
|---|---|---|---|---|---|---|
| | Run 1 | | | Run 2 | | |
| Sample | Initial Vis.(cP) | Final Vis.(cP) | Vis. Loss (%) | Initial Vis.(cP) | Final Vis. (cP) | Vis. Loss (%) |
| 1 | 3150 | 3300 | <0 | 3200 | 3400 | <0 |
| 2 | 3250 | 3600 | <0 | 3300 | 3800 | <0 |
| 3 | 3250 | 3750 | <0 | 3100 | 3550 | <0 |
| 4 | 3200 | 3800 | <0 | 3200 | 3700 | <0 |
| HEC Control | 3900 | 4500 | <0 | 3900 | 4550 | <0 |
| Positive Control | 3100 | 600 | 80.6 | 3100 | 550 | 82.3 |

EXAMPLE 4

Toothpaste Formulation

The cellulas-free xanthan gum of this invention is used in the following toothpaste formulations:

| Ingredients | Amount (gm) |
|---|---|
| Cellulase-Free Xanthan Gum | 0.50 |
| Sorbitol | 12.50 |
| Dicalcium phosphate dihydrate | 45.00 |
| CMC (medium viscosity) | 0.50 |
| Sodium lauryl sulfate | 1.50 |
| Saccharin | 0.15 |
| Flavor | 1.00 |
| Water | 26.35 (ml) |
| | 100.00 |

What is claimed is:

1. A process for producing cellulase-free xanthan gum which comprises:
   a. reacting xanthan gum beer at a pH of about 6.0 to about 7.0 with an alkali metal hypochlorite, and b. heating the product of step a at 85°–95° C. for 2–10 minutes.

2. The process of claim 1 wherein the hypochlorite level of the product of step a is below 0.03%.

3. The process of claim 1 wherein the hypochlorite level of the product of step a is below 0.02%.

4. A process for producing cellulase-free xanthan gum which comprises:
 a. reacting xanthan gum beer at pH 6.0 to 7.0 with 0.08–0.1 weight % sodium hypochlorite for 6–8 at about 30° C., and
 b. when the hypochlorite level of the product of step a is below 0.02% heating said product at 85°–95° C. for 2–10 minutes.

* * * * *